United States Patent
Allo et al.

(10) Patent No.: US 10,935,481 B2
(45) Date of Patent: Mar. 2, 2021

(54) METHOD AND SYSTEM FOR ESTIMATING BREAKDOWN PRESSURE USING ROCK WEAKNESS INDEX

(71) Applicant: CGG SERVICES SAS, Massy (FR)

(72) Inventors: Fabien Allo, Calgary (CA); Chi Vinh Ly, Katy, TX (US)

(73) Assignee: CGG SERVICES SAS, Massy (FR)

( * ) Notice: Subject to any disclaimer, the term of this patent is extended or adjusted under 35 U.S.C. 154(b) by 401 days.

(21) Appl. No.: 16/037,254

(22) Filed: Jul. 17, 2018

(65) Prior Publication Data

US 2020/0025667 A1    Jan. 23, 2020

(51) Int. Cl.
*G01N 15/08*    (2006.01)
*G01N 33/24*    (2006.01)

(52) U.S. Cl.
CPC ........... *G01N 15/088* (2013.01); *G01N 33/24* (2013.01); *G01N 2015/0846* (2013.01)

(58) Field of Classification Search
CPC .... E21B 49/005; G01N 23/083; G01N 15/00; G01N 15/08; G01N 15/0846; G01N 15/088; G01N 2015/0846; G01N 33/24; G01V 5/12; G01V 1/284
See application file for complete search history.

(56) References Cited

U.S. PATENT DOCUMENTS

| | | | |
|---|---|---|---|
| 9,613,253 B2 | 4/2017 | Ly et al. | |
| 2015/0301223 A1* | 10/2015 | Xu | G01V 1/50 703/2 |
| 2017/0016873 A1 | 1/2017 | Ly et al. | |
| 2017/0023689 A1* | 1/2017 | Spence | G01V 1/284 |
| 2017/0341981 A1* | 11/2017 | Pinkerton | C04B 28/02 |
| 2019/0301271 A1* | 10/2019 | Stolyarov | E21B 47/00 |

FOREIGN PATENT DOCUMENTS

WO    2018047009 A1    3/2018

OTHER PUBLICATIONS

Oliver et al., "Advanced cuttings analysis provides improved completion design, efficiency and well production," First Break vol. 24, No. 2, Feb. 1, 2016, pp. 69-76.*
Rickman et al. "A Practical Use of Shale Petrophysics for Stimulation Design Optimization: All Shale Plays Are Not Clones of the Barnett Shale", SPE International 2008.*

* cited by examiner

*Primary Examiner* — Catherine T. Rastovski
(74) *Attorney, Agent, or Firm* — Patent Portfolio Builders PLLC

(57) ABSTRACT

A method for estimating breakdown pressure values along a wellbore starts from analyzing cuttings from locations along the wellbore to determine rock properties, including rock texture information associated with the locations. The anisotropic elastic and mechanical properties at the locations are calculated based on the rock properties and using at least one rock physics model. Rock weakness index values corresponding to the locations are then calculated based on the anisotropic elastic and mechanical properties and the rock texture information. The breakdown pressure values at the locations are estimated from the rock weakness index values.

20 Claims, 5 Drawing Sheets

METHOD AND SYSTEM FOR ESTIMATING BREAKDOWN PRESSURE USING ROCK WEAKNESS INDEX

TECHNICAL FIELD

Embodiments of the subject matter disclosed herein generally relate to methods and systems for estimating breakdown pressure, more specifically, to using rock properties obtained by analyzing cuttings to predict the breakdown pressure.

DISCUSSION OF THE BACKGROUND

Knowledge of mechanical properties along lateral wellbores in unconventional oil and gas reservoirs (i.e., reservoirs from which oil and gas are recovered using fracking) is important for accurately appraising hydrocarbon potential and optimizing stage placement for hydraulic stimulation. A stage is an isolated portion typically of 120-250 feet of lateral wellbore where fluid under pressure is pumped through perforations to break the rock. It is desirable that the rock within the stage be homogenous in order to achieve consistent rock breakage. If the rock is heterogeneous, the portion of the stage made of softer rock would break first under increasing pressure leaving the other portion of the stage untreated leading to a sub-optimal hydrocarbon recovery.

Currently, oil and gas operators use wireline data logging tools to acquire petrophysical rock properties such as density, acoustic travel times and porosity. This data is then used to derive the mechanical and elastic properties of the rock such as bulk modulus, shear modulus, Young's modulus and Poisson's ratio along the logged wellbore.

For both cost and safety reasons, logging is usually not performed in horizontal wellbores drilled for production of unconventional reservoirs. U.S. Patent Application Publication No. 2017/0023689, which is incorporated herein by reference in its entirety describes a workflow for evaluating the elastic and mechanical properties based on cuttings analysis as an alternative to the wireline logging data. Cuttings are readily available as a byproduct of the drilling process. An appropriate rock physics model is applied to rock properties obtained from the cuttings analysis.

U.S. Pat. No. 9,613,253, which is incorporated herein by reference in its entirety, describes the use of scanning electron microscope-based (SEM) analysis for determining pore spaces within geologic material. PCT publication WO 2018/047009, which is also incorporated herein by reference in its entirety, discloses a workflow for the use of geologic indicators obtained from cuttings analysis for designing simulation operations.

U.S. Patent Application No. 2017/0016873, which is also incorporated herein by reference in its entirety, discloses a method for estimating a fracability index for a geological location. The fracability index is based on a fabric metric and a mineralogical composition metric determined for a geological sample extracted at a geological location. The fabric metric is a grain related measurement such as grain size or angularity, or a pore-space related measurement such as pore area, diameter, aspect ratio, and circumference, or statistics associated with such measurements. The mineralogical composition metric includes detecting a prevalence of at least one organic proxy within the geological sample such as vanadium, iron, uranium, thorium, copper, sulfur, zinc, chromium, nickel, cobalt, lead and molybdenum, and may also include detecting a prevalence of one, two, or all of siliciclastics, carbonate and clay.

In order to optimize hydraulic fracturing stage design, it is necessary to know the strengths (compressive and tensile) of the rock along the wellbore. These properties can be measured by applying pressure on a core or plug, but it is not a cost-effective technique to deliver the rock strengths along the full length of a wellbore. Models have been created to derive these strengths from log- or seismic-derived mechanical properties (e.g., Young's modulus and Poisson's ratio). However, the cost of acquiring those mechanical properties is high.

Therefore, there is a need to develop methods providing more direct and dense estimations of breakage pressure to assist in designing fracking operations and to avoid the wasteful trial-and-error approach of pumping all locations along a wellbore that has until now prevailed in hydraulic fracking.

SUMMARY

Various embodiments are based on a workflow using geologic indicators obtained from cuttings analysis for optimizing hydraulic fracking planning. In some embodiments, the rock physics model is improved to include vertical transverse isotropy (VTI) modeling, thereby allowing prediction of elastic properties of the rock in both the vertical and horizontal directions. In the case of a horizontal wellbore without logging data, the anisotropy factors are derived from the mineralogical and textural information extracted from the cuttings analysis. An improvement of the pore data interpretation is achieved by filtering and sorting the pore data gathered from cuttings to isolate planes of weakness. Weakness index values are calculated along the wellbore based on the predicted mechanical properties and the textural information extracted from the cuttings analysis. This index is an indicator of the force necessary to break the rock and, thus, the breakdown pressure. When a rock interval (stage) is subjected to an increasing pressure, the rock layer with the highest weakness index value breaks first, while layers with lower weakness index values require higher pressure to break down. The borehole breakdown pressure along the wellbore estimated based on the weakness index value is a useful indication of rock properties for stage and perforation placement.

According to an embodiment, there is a method improving exploitation of a wellbore. The method includes analyzing cuttings from locations along the wellbore to determine rock properties including rock texture information associated with the locations, calculating anisotropic elastic and mechanical properties at the locations based on the rock properties and using suitable rock physics models, calculating rock weakness index values corresponding to the locations, based on the anisotropic elastic and mechanical properties and the rock texture information, and estimating breakdown pressure values at the locations from the rock weakness index values. The exploitation is optimized based on the breakdown pressure values.

According to another embodiment there is system for improving exploitation of a wellbore. The system includes a sample preparation installation for preparing cuttings from locations along the wellbore for a scanning electron microscope with energy dispersive X-ray, SEM-EDX, analysis, an SEM-EDX apparatus for analyzing the prepared cuttings from locations to determine rock properties associated with the locations, and a data processing apparatus. The data processing apparatus is configured to calculate anisotropic elastic and mechanical properties at the locations based on the rock properties and using suitable rock physics models, to calculate rock weakness index values corresponding to the locations, based on the anisotropic elastic and mechanical properties and the rock texture information; and to estimate breakdown pressure values at the locations from the rock weakness index values.

According to yet another embodiment, there is a non-transitory computer readable recording media storing executable codes which when executed by a computer make the computer perform a method for improving exploitation of a wellbore. The method includes receiving images and data obtained by analyzing cuttings from locations along the wellbore to determine rock properties including rock texture information associated with the locations, calculating anisotropic elastic and mechanical properties at the locations based on the data and using suitable rock physics models, calculating rock weakness index values corresponding to the locations, based on the anisotropic elastic and mechanical properties and the rock texture information, and estimating breakdown pressure values at the locations from the rock weakness index values. The exploitation is optimized based on the breakdown pressure values.

BRIEF DESCRIPTION OF THE DRAWINGS

For a more complete understanding of the present inventive concept, reference is now made to the following descriptions taken in conjunction with the accompanying drawings, in which.

DETAILED DESCRIPTION OF THE INVENTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed using the terminology of geological analysis and fracking operations.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

The following embodiments use a tailor-made rock weakness index obtained from a combination of dry rock mechanical properties and textural information extracted from the cuttings to estimate breakdown pressure along a wellbore.

Figure 1:
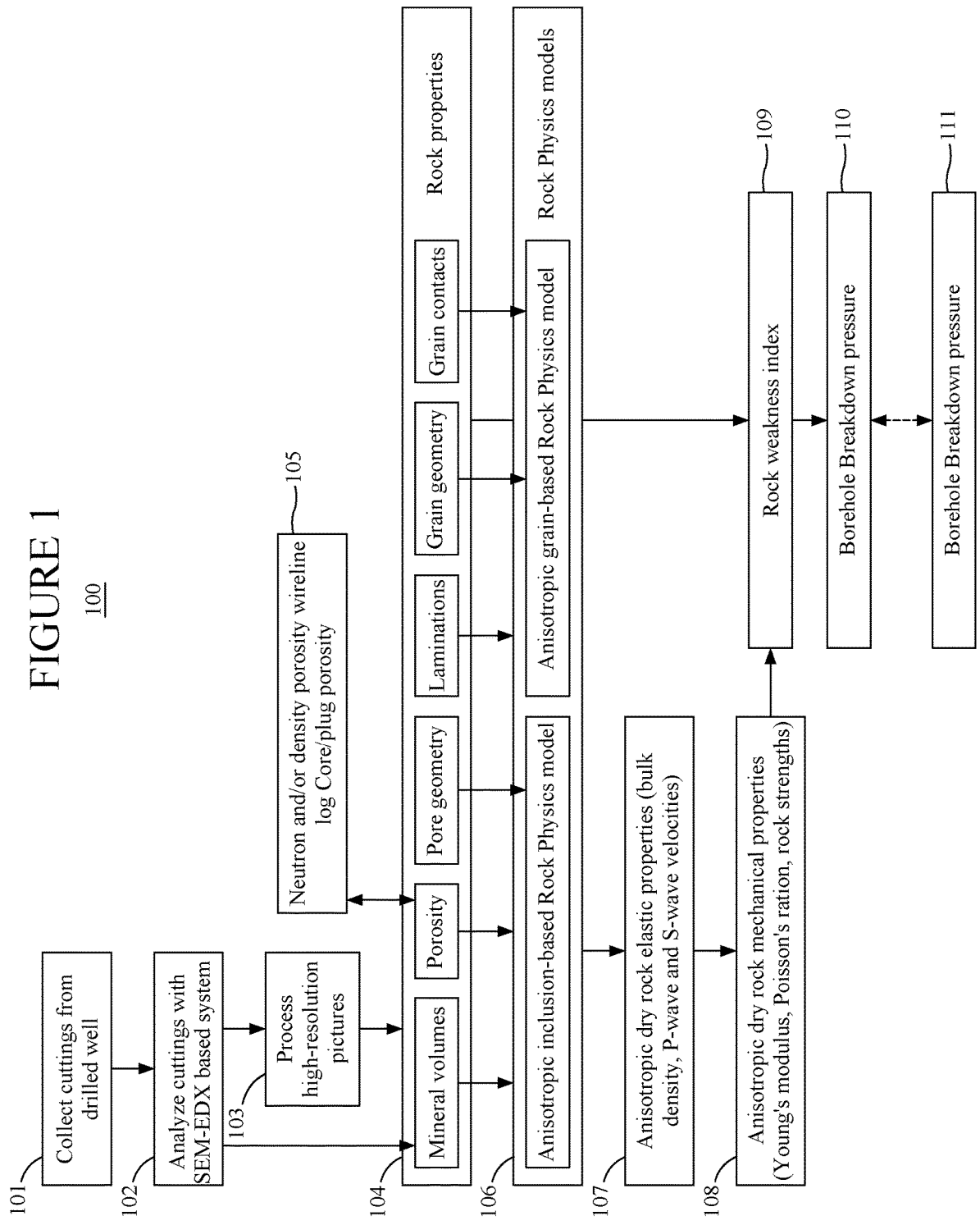
FIG. 1 illustrates workflow of a method of evaluating borehole breakdown pressures according to an embodiment.

FIG. 1 illustrates a workflow of a method 100 according to an embodiment. This figure provides a roadmap for the ensuing description. At 101, cuttings are collected from locations along the wellbore, for example, at about 30-ft. intervals (i.e., there are plural cutting locations along a stage length).

Figure 2:
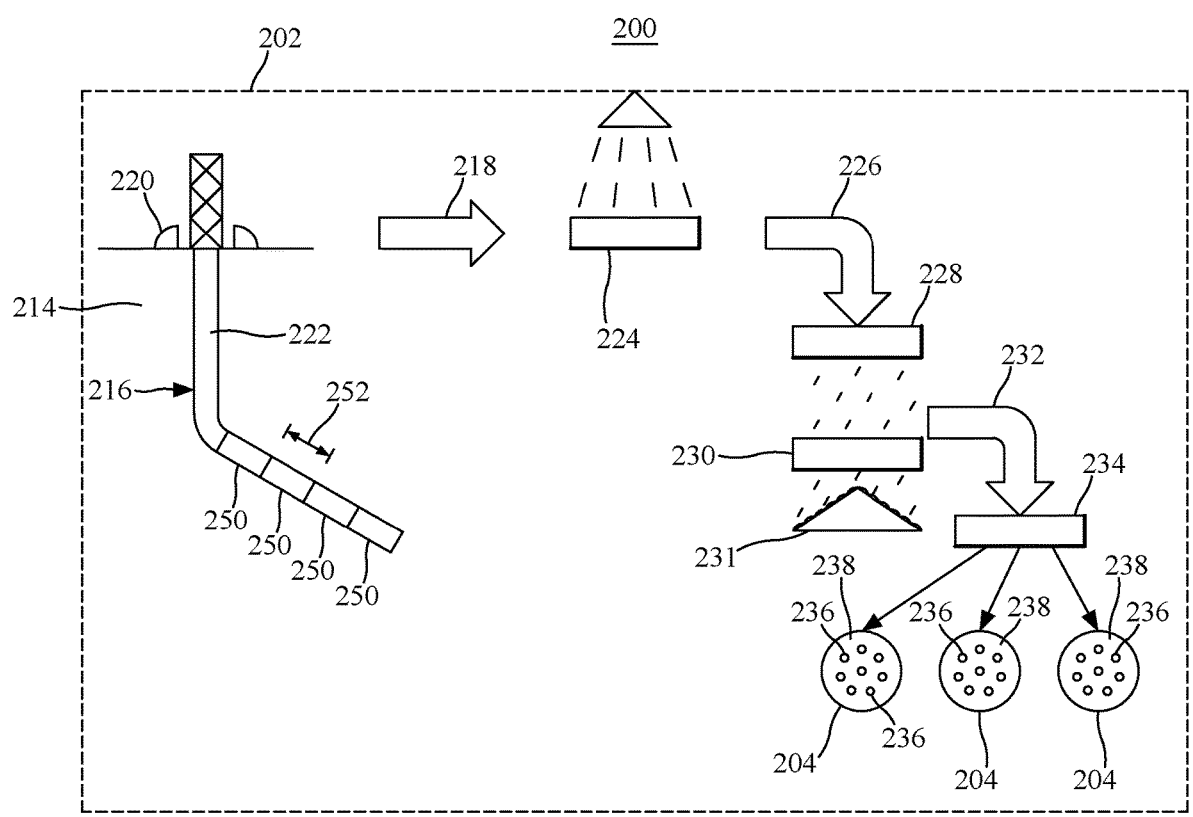
FIG. 2 illustrates a geological sampling mechanism.

FIG. 2 exemplarily illustrates an exploration process 200 including a geological sampling mechanism 202 to obtain a plurality of cuttings 204 for a subsurface 214 containing a wellbore 216. The wellbore may at first be vertical, but then deviates from vertical and may even become horizontal. Each cutting is obtained from a unique location 250 along the wellbore as the drill bit passes through the subsurface (e.g., an interval 252 between cutting locations). The geological material (including the cuttings) obtained from the subsurface during drilling is ejected at the surface (see piles 220) using either water or an oil-based fluid. Suitable cuttings include rock chips 222 generated during traditional wellbore or side-wall coring operations.

The geological material 218 is then processed to select the cuttings by first passing it through a washing station 224 using petrochemical fluids and water, as well as other organic and inorganic solvents and detergents, to produce cleaned geological material 226. Suitable washing stations and methods for cleaning the geological material are known. Then, the cleaned geological material 226 (which includes the cuttings) is passed through a coarse sieve 228 to remove all material equal to or greater than 2 mm in size, which can be referred to as cave-in material. The material of less than 2 mm in size is further passed through a finer sieve 230 that allows fine rock flour 231 to pass there-through if its size is less than about 0.06 mm (60 μm).

The remaining cleaned and sieved geological material 232, which is smaller than cave-in and larger than rock flour (i.e., contains particles in from about 0.06 mm to about 2 mm), is passed through a sample preparation system 234 to be prepared for analysis. The sample preparation system immobilizes the particles 236 in a polymerized plastic or resin block 238 and exposes a cross-sectional surface of one plane of the block. This exposes a cross-section of multiple geological particles 236.

Returning now to FIG. 1, at 102, the cuttings are analyzed with a Scanning Electron Microscopy (SEM) with Energy Dispersive X-Ray (EDX) system. The SEM-EDX analysis provides a relatively rapid, inexpensive, and basically non-destructive surface analysis.

High-resolution images 103 generated as part of the SEM-EDX analysis are then processed to identify the pore spaces within a geological sample with cuttings from a location. After identifying the pore spaces, the image may be filtered to remove pore spaces smaller than a given minimum threshold size to eliminate the small disconnected pores.

The filtered pore images are further processed to remove pore spaces with an aspect ratio above a predetermined maximum threshold value. A pore's aspect ratio is equal to the short axis length over the long axis length of the pore. This additional filtering aims to remove large ellipsoidal or circular pores.

The remaining pore spaces, which are large and elongated, are defined as planes of weakness or laminations. The number of laminations is one of the rock properties 104 obtained from the SEM-EDX analysis.

The SEM-EDX analysis and image processing yields geological rock data 104, including one or more of mineral volumes, macro-porosity, grain size, pore size, grain geometry, the pore and grain aspect ratio and number of weakness planes. Quantitative information about the mineralogy (for example but not limited to the volume of clays including illite, which is characterized by a relatively strong intrinsic anisotropy) and textural information (for example, the number of weakness planes that have opened in the cuttings during the drilling process) may be combined to derive an estimation of the compressional and shear velocity anisotropy factors ($\varepsilon$ and $\gamma$ respectively).

If measured porosity data like neutron and/or density porosity wireline logs or core plug porosity data is available, it can be used at 105 to calibrate the porosity derived from the mineralogical/textural data obtained from SEM-EDX analysis (i.e., a comparison for quality control). The latter is usually an overestimation of the actual in-situ porosity because the rock material might have been damaged (additional cracks) due to the drop of effective pressure on the cuttings when brought back to the surface, which causes an increased pore volume.

Porosity is important in the model, and differences in porosity values exist between wireline and direct analysis of the geologic material due to the different nature of the techniques. A better correlation is observed between mechanical properties estimated in the traditional way using sonic and density data and the models proposed when wireline porosity is used. It is therefore highly recommended to calibrate the porosity estimated from the analysis of the rock material with available porosity logs if possible (in vertical wellbores, for example).

The rock properties gathered through the steps outlined above are then input into the most suitable rock physics model based on the type of rock being analyzed and the available data at 106. In one embodiment, an anisotropic inclusion-based rock physics model may be used as described in U.S. Patent Application Publication No. 2017/0023689. In another embodiment, an anisotropic grain-based rock physics model may be used. Other models may be used as suitable.

In more detail, as described in U.S. Patent Application Publication No. 2017/0023689, rock physics models utilize a three-step process to generate the desired mechanical and elastic properties of the subsurface form the input rock properties. In the first step, the effective mineral properties of the rock, e.g., density, bulk modulus and shear modulus, are computed based on a weighted average of the different mineral constituents. Commonly used equations for these computations include, but are not limited to, the Voigt upper bound, $M_V = \Sigma_i f_i M_i$, the Reuss lower bound, $$M_R = \left| \sum_i \frac{f_i}{M_i} \right|^{-1},$$

the Hashin-Shtrikman bounds, $$K_{HS}^{\pm} = K_1 + \frac{f_2}{(K_2 - K_1)^{-1} + f_1 \left( K_1 + \frac{4}{3}\mu_1 \right)^{-1}} \text{ and}$$

$$\mu_{HS}^{\pm} = \mu_1 + \frac{f_2}{(\mu_2 - \mu_1)^{-1} + 2f_1(K_1 + 2\mu_1) / \left[ 5\mu_1 \left( K_1 + \frac{4}{3}\mu_1 \right) \right]},$$

and combinations of these equations, for example, the Voigt-Reuss-Hill average, $$M_H = \frac{M_V + M_R}{2}.$$

In the second step, the dry rock properties, i.e., dry rock bulk and shear modulus, of the subsurface rock are calculated by integrating the effect of the pore space geometry and contacts between the different rock constituents. This calculation is made using two main types of models, grain-based models and inclusion-based models. Grain-based models are derived from the Hertz-Mindlin model, $$K_{dry} = \left[ \frac{C^2(1-\phi)^2 \mu_m^2}{18\pi^2(1-v_m)^2} P_{eff} \right]^{1/3} \text{ and}$$

$$\mu_{dry} = \frac{5 - 4v_m}{5(2 - v_m)} \left[ \frac{3C^2(1-\phi)^2 \mu_m^2}{2\pi^2(1-v_m)^2} P_{eff} \right]^{1/3},$$

which defines the rock frame elasticity based on the effective pressure, the porosity, the number of contacts between grains and the grain elastic properties. Inclusion-based models are derived from the Kuster-Toksöz model, $$(K_{dry} - K_m) \frac{\left( K_m + \frac{4}{3}\mu_m \right)}{\left( K_{dry} + \frac{4}{3}\mu_m \right)} = \sum_i f_i(K_i - K_m)P(\alpha)^i,$$

$$(\mu_{dry} - \mu_m) \frac{(\mu_m + \xi_m)}{(\mu_{dry} + \xi_m)} = \sum_i f_i(\mu_i - \mu_m)Q(\alpha)^i \text{ with}$$

$$\xi_m = \frac{\mu(9K_m + 8\mu_m)}{6(K_m + 2\mu_m)},$$

which defines the rock frame elasticity based on the geometry of the pore space idealized as ellipsoids of a given aspect ratio.

In the third step, the saturated rock properties are computed by performing a fluid substitution, i.e., the addition of a given fluid in the pore space. The most commonly used model was developed by Gassmann, $$K_{sat} = K_{dry} + \frac{(1 - K_{dry}/K_m)^2}{\phi/K_{fl} + (1-\phi)/K_m - K_{dry}/K_m^2}$$

and $\mu_{sat} = \mu_{dry}$, but is only valid when the pore-filling material is a fluid with zero shear modulus. Ciz and Shapiro have later generalized the equations to account for a solid pore-filling material. The fluid properties required for the substitution can be measured in laboratory or computed from empirical equations like Batzle & Wang and the FLAG consortium models.

As used in these models, M refers to the elastic modulus (bulk or shear), and K refers to the bulk modulus. The shear modulus is indicated as $\mu$, and the mineral volume fraction is f. The effective pressure is $P_{eff}$, while the effective porosity is $\phi$. Poisson's Ratio is given by $v$, and $P(\alpha)$ and $Q(\alpha)$ indicate pore shape factors depending on the pore aspect ratio $\alpha$. The subscripts used in the equation are m for a mineral property, fl for a fluid property, dry for a dry rock property and sat for a saturated rock property.

Unconventional reservoirs, which are stimulated via hydraulic fracturing are characterized by anisotropic elastic behavior due to their composition (which includes intrinsically anisotropic minerals like illite and other clay minerals) and their texture (horizontal laminations due to the process of sedimentation that drove the creation of those rocks). Therefore, anisotropy has to be taken into account because acoustic wave (compressional and shear) velocities are significantly different in vertical and horizontal directions. The calibration of the rock physics model is usually performed based on selected vertical wells where both log and cuttings data are available. But the velocities recorded at a particular depth along those vertical wellbores are different from the velocities that would be recorded along a horizontal wellbore at that same depth. The horizontal velocities would be substantially faster than the vertical ones due to the rock anisotropy. The velocity anisotropy factors $\varepsilon$ and $\gamma$ can be derived from the mineralogical and textural information extracted from cuttings in order to reliably predict velocities along the horizontal wellbores.

$$\varepsilon = a_\varepsilon \overline{V_{clay}} + b_\varepsilon \overline{WPC} \quad (1)$$

$$\gamma = a_\gamma \overline{V_{clay}} + b_\gamma \overline{WPC} \quad (2)$$

where $\varepsilon$ is the P-wave velocity anisotropy factor, $\gamma$ is the S-wave velocity anisotropy factor, $\overline{V_{clay}}$ is the clay volume averaged over a given interval (3 stage lengths, for example), $\overline{WPC}$ is the weakness planes count averaged over a given interval (3 stage lengths, for example), and $a_\varepsilon$, $b_\varepsilon$, $a_\gamma$, $b_\gamma$ are constants that are calibrated. The averaging is needed to remove some of the "noise" in the cuttings data. WPC in particular exhibit high frequency variations. On one hand, only a fraction of the cuttings sampled at a particular depth, are analyzed, so the measurements are biased because the same measurements on another fraction of cuttings coming from the same depth may yield different values. On the other hand, only the average properties are really meaningful (one depth has more weakness planes than another one). Since measurements at the same depth are not repeated, the high frequency noise is removed by averaging the measurements over a given length to extract the low frequency trend.

In the context of horizontally laminated medium, the relationship between the vertical/slow and horizontal/fast compression and shear velocities is given by:

$$v_{ph} = v_{pv}\sqrt{1+2\varepsilon} \quad (3)$$

$$v_{sh} = v_{sv}\sqrt{1+2\gamma} \quad (4)$$

where the P-wave anisotropy factor is $$\varepsilon = \frac{c_{11} - c_{33}}{2c_{33}} \quad (5)$$

and the S-wave anisotropy factor is $$\gamma = \frac{c_{44} - c_{66}}{2c_{44}} \quad (6)$$

with $c_{11}$ is a density-dependent P-wave modulus along the horizontal direction, $c_{33}$ a density-dependent P-wave modulus along the vertical direction, $c_{44}$ a density-dependent S-wave modulus along the horizontal direction, and $c_{66}$ a density-dependent S-wave modulus along the vertical direction. Here, for a density $\beta$, $c_{11} = \rho V_{PH}^2$ is P-wave modulus along the horizontal direction, $c_{33} = \rho V_{PV}^2$ is P-wave modulus along the vertical direction, $c_{44} = \rho V_{SH}^2$ is S-wave modulus along the horizontal direction, and $c_{66} = \rho V_{SV}^2$ is P-wave modulus along the vertical direction.

The rock physics models may not take into account the in-situ stresses, which have an effect on the in-situ mechanical properties. A correction can be applied to the results of the models if the in-situ stresses are known. However, this in-situ stresses data is not obtained from SEM-EDX analysis of rock at the surface, but from a priori information based on laboratory tests and/or regional stress field measurements or estimates.

Returning now to FIG. 1, the rock physics model outputs the elastic properties (bulk density, P-wave and S-wave velocities) of the dry rock in the vertical (slow velocities) and horizontal (fast velocities) directions at 107. These values can be combined to compute derived elastic attributes like impedances and velocity ratio.

Then, mechanical properties (such as Young's modulus, Poisson's ratio, compressive and tensile strengths) of the dry rock can be estimated from the elastic properties at 108.

At 109, a rock weakness index is computed based on the estimated mechanical properties and the rock texture information such as (but not limited to) the number of weakness planes.

If the stage design is already available, the weakness index can be averaged per stage. Minimum and maximum weakness indices can also be computed per stage. The difference between these two extreme values can be used as an indicator of the rock heterogeneity per stage. This can be directly related to stimulation efficiency because a homogeneous stage is stimulated more efficiently than a heterogeneous one.

For example, in one embodiment, the weakness index WI (which may be expressed as a percentage) is calculated using the following formula:

$$WI(\%) = \frac{YM_{max} - YM}{2(YM_{max} - YM_{min})} + \frac{PR_{max} - PR}{2(PR_{max} - PR_{min})} + \frac{\overline{WPC}}{c} \quad (7)$$

where YM is the dry rock Young's modulus value, $YM_{min}$ is the minimum dry rock Young's modulus value over the interval of interest, $YM_{max}$ is the maximum dry rock Young's modulus over the interval of interest, PR is the dry rock Poisson's ratio value, $PR_{min}$ is the minimum dry rock Poisson's ratio value over the interval of interest, $PR_{max}$ is the maximum dry rock Poisson's ratio over the interval of interest and $\overline{WPC}$ is the weakness planes count averaged over a given interval (3 stage lengths, for example) and c is a constant that is calibrated. For example, the interval of interest may be the full length of the wellbore being analyzed. The weakness index is based on relative values, not absolute ones and therefore are not directly comparable from one wellbore to another. The advantage of using relative values is that weakness index's range is 0 to 100% thus increasing the amplitude of the variations of the index. If absolute values (like 0 for YMmin, 100 for YMmax, 0 for PRmin, 0.5 for PRmax) were used, weakness index values values would be comparable from one wellbore to another (indicating in which wellbore the rock is softer/harder), but the range would be smaller and the variations potentially difficult to see. For example, if YM actually varies from 30 to 40 and PR from 0.2 to 0.3, weakness index values would only vary from 50 to 65% (instead of 0-100 with relative values) thereby reducing the variation range with 85%. Note that variations of the above formula may be used for calculating weakness index values.

At 110 the borehole breakdown pressure is estimated using the weakness index. In one embodiment, the borehole breakdown pressure is a linear function of the weakness index:

$$BP(psi)=a \times WI(\%)+b \qquad (8)$$

where BP(psi) is the rock breakdown pressure in psi, WI (%) is the rock weakness index in percent, a, b: constants calibrated using measurements.

The relationship between the borehole breakdown pressure and the weakness index can be derived statistically (e.g., using linear regression) using the weakness index computed at 109. If the weakness index has been averaged per stage at 109, average, minimum and maximum breakdown pressures per stage can also be computed. The difference between the minimum and maximum breakdown pressures provide an uncertainty around the average breakdown pressure.

Once the wellbore has undergone hydraulic fracturing, the estimated borehole breakdown pressure can be compared with the measured borehole breakdown pressure (i.e., drilling data) at 111 to evaluate the accuracy of the estimation.

Data used for consistency checking and calibration or quality control is emphasized in the right top corner of FIG. 1.

Figure 3:
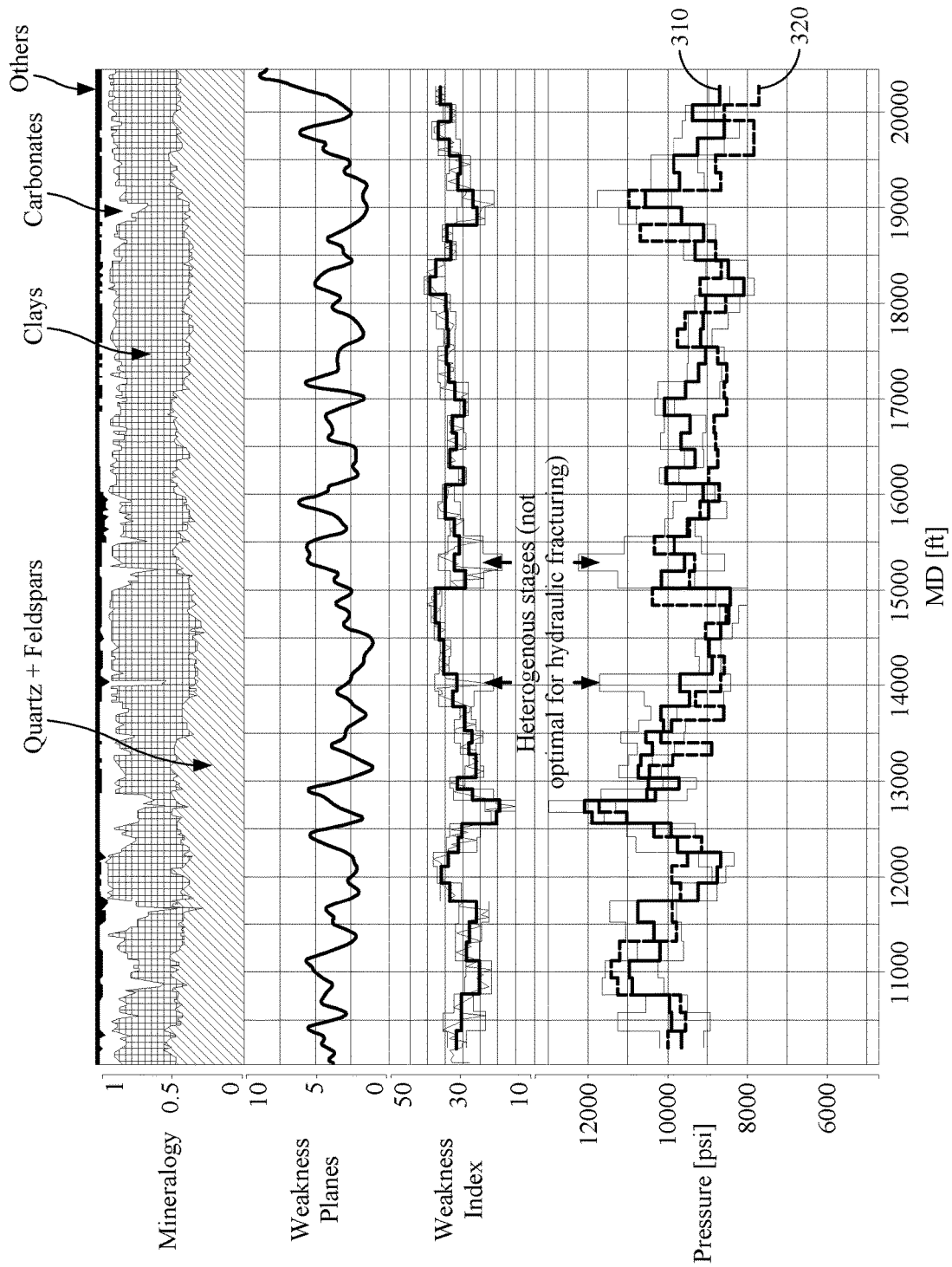
FIG. 3 is a series of related graphs illustrating results of a method according to an embodiment.

FIG. 3 is a series of related graphs (having the same horizontal axis, length along the wellbore) illustrating the results of the above-described approach. The top graph illustrates mineralogic composition (clays, quartz and feldspars, carbonates or others) of the cuttings. The second graph represents the number of weakness planes in the cuttings. The third graph is the weakness index with an associated interval per stage. Heterogeneous stages, which are expected to be inefficiently stimulated, are characterized by large difference between the minimum and maximum weakness index value. The fourth graph represents the breakdown pressure 310 as estimated with the associated range and as measured 320.

The main benefit of obtaining an estimate of breakdown pressure in this manner is that it provides a cost-effective, non-destructive and non-intrusive way of highlighting stages that would not be efficiently stimulated before the wellbore is actually hydraulically fractured. The predicted breakdown pressure can help improving the design of the stages to maximize their homogeneity in terms of mechanical properties and avoid unproductive stages. It can also help drilling engineers better plan the equipment (pump capacity) needed for the hydraulic fracturing exploitation process.

Figure 4:
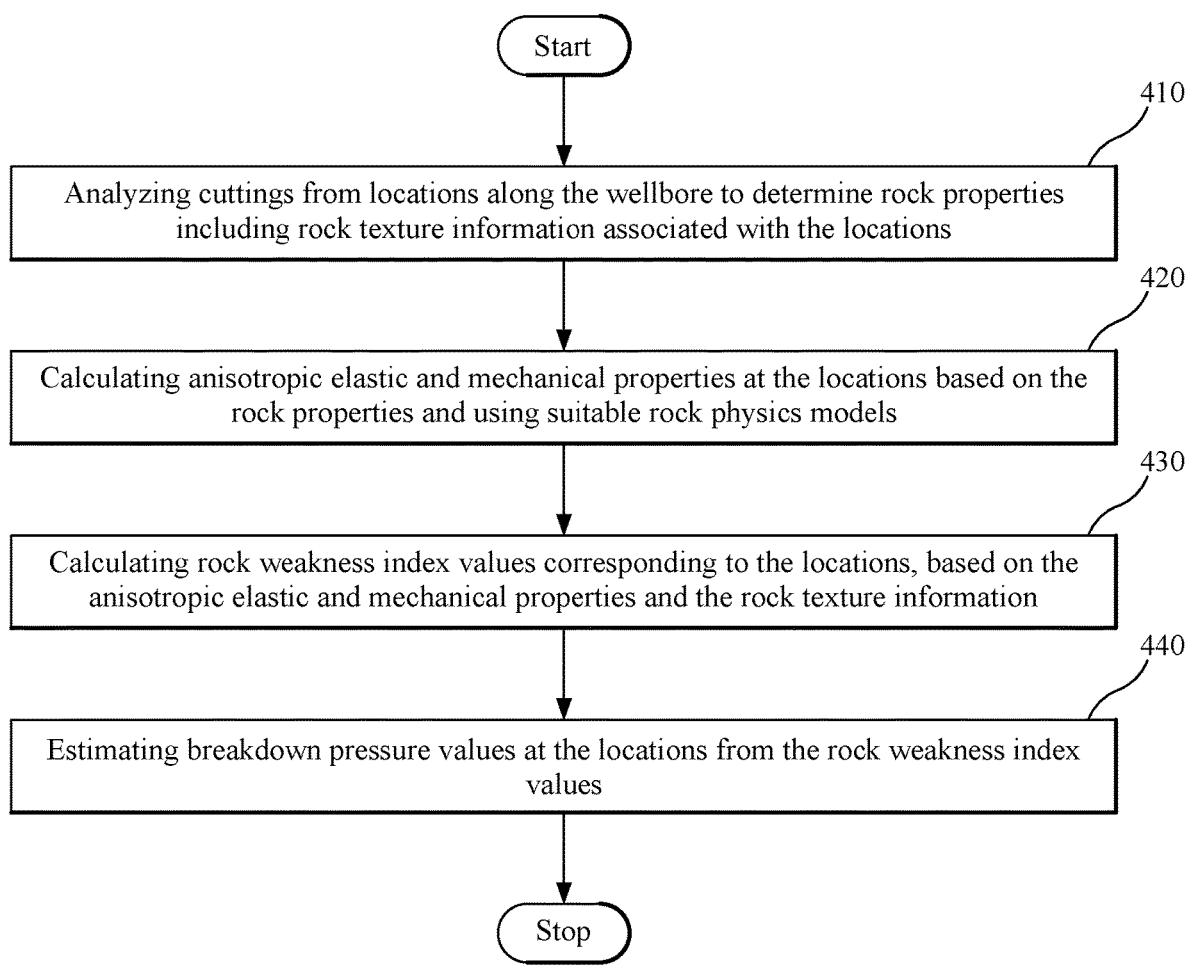
FIG. 4 is a flowchart of a method according to an embodiment.

FIG. 4 is a flowchart of a method 400 according to an embodiment. Method 400 includes analyzing cuttings from locations along the wellbore to determine rock properties including rock texture information associated with the locations at 410, calculating anisotropic elastic and mechanical properties at the locations based on the rock properties and using suitable rock physics models, at 420, and calculating rock weakness index values corresponding to the locations, based on the anisotropic elastic and mechanical properties and the rock texture information, at 430. Method 400 then includes estimating breakdown pressure values at the locations from the rock weakness index values at 440.

The cuttings may be analyzed using a scanning electron microscope with energy dispersive X-ray, SEM-EDX, analysis to yield high resolution images. The rock texture information may include a number of weakness planes obtained by counting large elongated pore spaces in an SEM-EDX image.

In one embodiment, calculating the anisotropic elastic and mechanical properties includes obtaining first values including bulk density, P-wave and S-wave velocities, and deriving second values including the Young's modulus and Poisson's ratio form the first values. The rock weakness index values may be calculated using formula (7). The breakdown pressure may be calculated using linear relationship (8) calibrated with breakdown pressure measurements.

The breakdown pressure values may be used to optimize stage placement in the wellbore, e.g., for avoiding heterogeneous stages. Log, core and/or plug data may be used for checking the consistency of the estimated breakdown pressure values.

Figure 5:
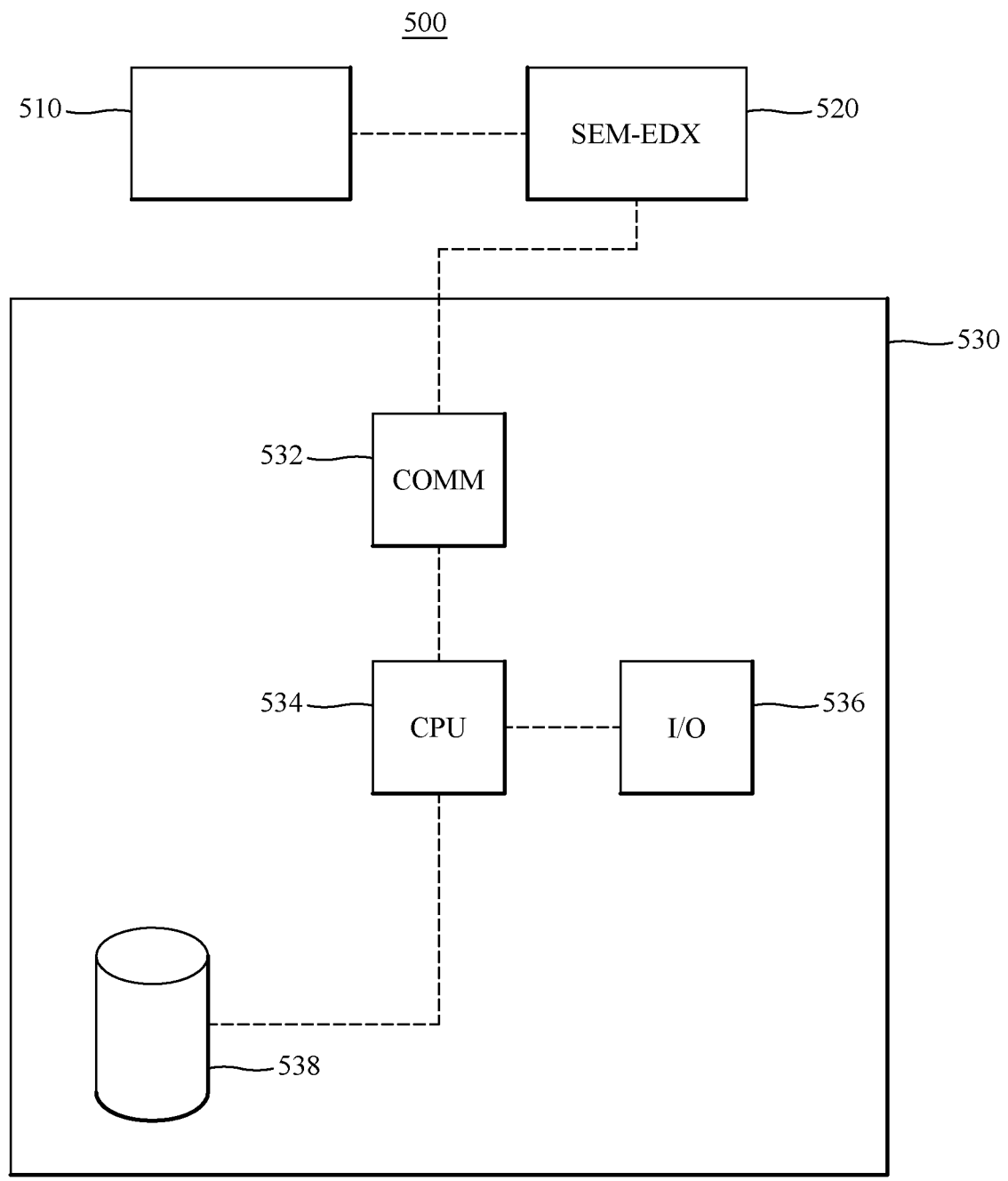
FIG. 5 is a block diagram of a system according to an embodiment.

FIG. 5 is a block diagram of a system 500 according to an embodiment. The system includes a sample preparation installation 510 for preparing cuttings from locations along the wellbore for a SEM-EDX analysis, an SEM-EDX apparatus 520 for analyzing the prepared cuttings from locations to determine rock properties associated with the locations, and a data processing apparatus 530.

The data processing apparatus includes an interface 532 for receiving the rock properties data and a central processing unit 534 including at least one processor. The processor calculates anisotropic elastic and mechanical properties at the locations based on the rock properties and using suitable rock physics models, and then calculates rock weakness index values corresponding to the locations, based on the anisotropic elastic and mechanical properties and the rock texture information, to then estimate breakdown pressure values at the locations from the rock weakness index values.

Data processing apparatus 530 may also include a user interface 536 and a memory 538. The memory may store executable codes that make the central processing unit to execute a method like the ones described in this document.

The disclosed embodiments provide methods and systems for estimating breakdown pressure based on a rock weakness index. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A method for improving exploitation of a wellbore, the method comprising:

analyzing cuttings from locations along the wellbore to determine rock properties including rock texture information associated with the locations;

calculating anisotropic elastic and mechanical properties at the locations based on the rock properties and using at least one rock physics model;

calculating rock weakness index values corresponding to the locations, based on the anisotropic elastic and mechanical properties and the rock texture information; and estimating breakdown pressure values at the locations from the rock weakness index values, wherein the exploitation is optimized based on the breakdown pressure values.

2. The method of claim 1, wherein the cuttings are analyzed using a scanning electron microscope with energy dispersive X-ray, SEM-EDX, analysis to yield high resolution images.

3. The method of claim 2, wherein the rock texture information includes a number of weakness planes obtained by counting large elongated pore spaces in an SEM-EDX image.

4. The method of claim 1, wherein calculating the anisotropic elastic and mechanical properties includes
obtaining first values including bulk density, P-wave and S-wave velocities, and
deriving second values including the Young's modulus and Poisson's ratio from the first values.

5. The method of claim 4, wherein the weakness index WI values are calculated as:

$$WI(\%) = \frac{YM_{max} - YM}{2(YM_{max} - YM_{min})} + \frac{PR_{max} - PR}{2(PR_{max} - PR_{min})} + \frac{\overline{WPC}}{c}$$

where YM is a dry rock Young's modulus value, $YM_{min}$ is a minimum dry rock Young's modulus value over an interval of interest, $YM_{max}$ is a maximum dry rock Young's modulus value over the interval of interest, PR is a dry rock Poisson's ratio value, $PR_{min}$ is a minimum dry rock Poisson's ratio value over the interval of interest, $PR_{max}$ is a maximum dry rock Poisson's ratio value over the interval of interest and $\overline{WPC}$ is the weakness planes count averaged over a predetermined interval and c is a constant.

6. The method of claim 1, wherein the breakdown pressure values are derived from the rock weakness index values through a linear relationship.

7. The method of claim 1, further comprising:
using the breakdown pressure values to optimize stage placement in the wellbore for avoiding heterogeneous stages.

8. The method of claim 1 further comprising:
using log, core and/or plug data for consistency check.

9. A system for improving wellbore exploitation, the system comprising:
a sample preparation installation for preparing cuttings from locations along the wellbore for a scanning electron microscope with energy dispersive X-ray, SEM-EDX, analysis;
an SEM-EDX apparatus for analyzing the prepared cuttings from locations to determine rock properties associated with the locations;
a data processing apparatus with a processor configured
to calculate anisotropic elastic and mechanical properties at the locations based on the rock properties and using at least one rock physics model,
to calculate rock weakness index values corresponding to the locations, based on the anisotropic elastic and mechanical properties and the rock texture information; and
to estimate breakdown pressure values at the locations from the rock weakness index values.

10. The system of claim 9, wherein the SEM-EDX apparatus yields high resolution images used to count large elongated pore spaces indicating weakness planes at the locations, respectively.

11. The system of claim 9, wherein the data processing apparatus calculates the anisotropic elastic and mechanical properties by
obtaining first values including bulk density, P-wave and S-wave velocities, and
deriving second values including the Young's modulus and Poisson's ratio from the first values.

12. The system of claim 10 wherein the data processing apparatus calculates the weakness index WI values as:

$$WI(\%) = \frac{YM_{max} - YM}{2(YM_{max} - YM_{min})} + \frac{PR_{max} - PR}{2(PR_{max} - PR_{min})} + \frac{\overline{WPC}}{c}$$

where YM is a dry rock Young's modulus value, $YM_{min}$ is a minimum dry rock Young's modulus value over an interval of interest, $YM_{max}$ is a maximum dry rock Young's modulus value over the interval of interest, PR is a dry rock Poisson's ratio value, $PR_{min}$ is a minimum dry rock Poisson's ratio value over the interval of interest, $PR_{max}$ is a maximum dry rock Poisson's ratio value over the interval of interest and WPC is the weakness planes count averaged over a predetermined interval and c is a constant.

13. The system of claim 9, wherein the breakdown pressure values are derived from the rock weakness index values through a linear relationship.

14. The system of claim 9, wherein the data processing apparatus uses the borehole breakdown pressure values to optimize stage placement in the wellbore for avoiding heterogeneous stages.

15. The system of claim 9, wherein the data processing apparatus uses using log, core and/or plug data for consistency check of the estimated breakdown pressure values.

16. A non-transitory computer readable recording media storing executable codes which when executed by a computer make the computer perform a method for improving exploitation of a wellbore, the method comprising:
receiving images and data obtained by analyzing cuttings from locations along the wellbore to determine rock properties including rock texture information associated with the locations;
calculating anisotropic elastic and mechanical properties at the locations based on the data and using at least one rock physics models;
calculating rock weakness index values corresponding to the locations, based on the anisotropic elastic and mechanical properties and the rock texture information; and
estimating breakdown pressure values at the locations from the rock weakness index values, wherein the exploitation is optimized based on the breakdown pressure values.

17. The non-transitory computer readable recording media of claim 16, wherein the cuttings are analyzed using a scanning electron microscope with energy dispersive X-ray, SEM-EDX, analysis to yield high resolution images.

18. The non-transitory computer readable recording media of claim 17, wherein the rock texture information includes a number of weakness planes obtained by counting large elongated pore spaces in an SEM-EDX image.

19. The non-transitory computer readable recording media of claim 16, wherein calculating the anisotropic elastic and mechanical properties includes
obtaining first values including bulk density, P-wave and S-wave velocities, and
deriving second values including the Young's modulus and Poisson's ratio from the first values.

20. The non-transitory computer readable recording media of claim 19, wherein the weakness index WI values are calculated as:

$$WI(\%) = \frac{YM_{max} - YM}{2(YM_{max} - YM_{min})} + \frac{PR_{max} - PR}{2(PR_{max} - PR_{min})} + \frac{\overline{WPC}}{c}$$

where YM is a dry rock Young's modulus value, $YM_{min}$ is a minimum dry rock Young's modulus value over an interval of interest, $YM_{max}$ is a maximum dry rock Young's modulus value over the interval of interest, PR is a dry rock Poisson's ratio value, $PR_{min}$ is a minimum dry rock Poisson's ratio value over the interval of interest, $PR_{max}$ is a maximum dry rock Poisson's ratio value over the interval of interest and $\overline{WPC}$ is the weakness planes count averaged over a predetermined interval and c is a constant.

\* \* \* \* \*